(12) United States Patent
Whitmore et al.

(10) Patent No.: US 6,699,484 B2
(45) Date of Patent: Mar. 2, 2004

(54) FIBRIN SEALANTS OR ADHESIVES COMPRISING A HYALURONIC ACID DERIVATIVE MATERIAL

(75) Inventors: Elaine Whitmore, Bradenton, FL (US); Marc R. Paquin, Sarasota, FL (US)

(73) Assignee: Haemacure Corporation, Montreal (CA)

( * ) Notice: Subject to any disclaimer, the term of this patent is extended or adjusted under 35 U.S.C. 154(b) by 0 days.

(21) Appl. No.: 10/336,936

(22) Filed: Jan. 6, 2003

(65) Prior Publication Data

US 2003/0103961 A1 Jun. 5, 2003

Related U.S. Application Data

(63) Continuation of application No. 09/554,745, filed as application No. PCT/US98/24605 on Nov. 17, 1998, now Pat. No. 6,503,527.
(60) Provisional application No. 60/065,884, filed on Nov. 17, 1997.

(51) Int. Cl.$^7$ .............................. A61K 9/00; A61K 9/08; A61L 25/00
(52) U.S. Cl. ........................ 424/400; 424/422; 424/424; 424/425; 424/426; 424/443; 424/444; 514/21; 514/54; 514/55; 514/56; 606/214; 606/215
(58) Field of Search .............................. 424/400, 422, 424/424, 425, 426, 443, 444; 514/21, 54, 55, 56; 606/214, 215

(56) References Cited

U.S. PATENT DOCUMENTS

| | | |
|---|---|---|
| 4,650,678 A | 3/1987 | Fuhge et al. |
| 4,851,521 A | 7/1989 | della Valle et al. |
| 4,909,251 A | 3/1990 | Seelich |
| 4,957,744 A | 9/1990 | della Valle |
| 5,202,431 A | 4/1993 | della Valle |
| 5,290,918 A | 3/1994 | Bui-Khac |
| 5,336,767 A | 8/1994 | della Valle et al. |
| 5,395,923 A | 3/1995 | Bui-Khac et al. |
| 5,631,011 A | 5/1997 | Waldstrom |
| 5,773,033 A | 6/1998 | Cochrum et al. |
| 6,503,527 B1 * | 1/2003 | Whitmore et al. ........... 424/422 |

FOREIGN PATENT DOCUMENTS

| | | |
|---|---|---|
| EP | 0 216 453 A2 | 4/1987 |
| WO | WO96/17631 | 6/1996 |

OTHER PUBLICATIONS

Andrião–Escarso, S., et al., "Isolation and Characterization of a New Clotting Factor From *Bothrops Jararacussu* (Jararacucu) Venom". *Toxicon*, 35: 1043–1052 (1997).

Benedetti, L., "New Biomaterials from Hyaluronic Acid", *Medical Device Technology*, 32–37 (Nov. 1994).

Brennan, M., "Fibrin Glue", *Blood Reviews*, 5: 240–244 (1991).

Chisholm, R., et al., "Fibrin Sealant as a Plug for the Post Liver Biopsy Needle Track", *Clinical Radiology*, 40: 627–628 (1989).

Dascombe, W., et al., "Application of Thrombin Based Fibrin Glue and Non–Thrombin Based Batroxobin Glue on Intact Human Blood Vessels: Evidence for Transmural Thrombin Activity", *Thromb. Haemost.*, 78:947–951 (1997).

Fořtová, H., et al., "Simultaneous Isolation of Protein C Activator, Fibrin Clot Promoting Enzyme (Fiprozyme) and Phospholipase $A_2$ from the Venom of the Southern Copperhead Snake", *J. Chromatogr.* S. Biomed Appl. 694: 49–53 (1997).

Hahn, B., et al., "Purification and Molecular Cloning of Calobin, a Thrombin–Like Enzyme from Agkistrodon Caliginosus (Korean Viper)", *J. Biochem.* (Tokyo) 119: 835–843 (1996).

Kjaergard, H., et al., "Autologous Fibrin Glue Preparation and Clinical Use in Thoracic Surgery", *Eur., J. Cardio–Thorc. Surg.* 6: 52–54 (1992).

Rathke T., et al., "Review of Chitin and Chitosan as Fiber and Film Formers", *Rev. Macromol. Chem. Phys.* C34 (3): 375–437 (1994).

Stechison, M., "Rapid Polymerizing Fibrin Glue from Autologous or Single–Donor Blood: Preparation and Indications", *J. Neurosurgery* 76: 626–628 (1992).

Thompson, D., et al., "Fibrin Glue: A Review of Its Preparation, Efficacy, and Adverse Effects as a Topical Hemostat", *Drug Intelligence and Clinical Pharmacy*, 22:946–952 (1998).

Toma, A., et al., "Autologous Fibrin Glue in the Repair of Dural Defects in Craniofacial Resections", *J. Laryngology and Otology*, 106: 356–357 (1992).

* cited by examiner

*Primary Examiner*—Nathan M. Nutter
(74) *Attorney, Agent, or Firm*—Michael Best & Friedrich, LLP; Teresa J. Welch, Esq.; Charlene L. Yager, Esq.

(57) ABSTRACT

An especially useful fibrin glue composition comprises a biocompatible, bioabsorbable hyaluronic acid derivative material, upon which are applied or chemically bonded fibrinogen and thrombin, along with other optional constituents, such as additional coagulation factors, antifibrinolytics, stabilizers and biologically active substances. The fibrinogen, thrombin and other components can take the form of a dry preparation, an aqueous or nonaqueous preparation, or as a combination thereof. Such a fibrin glue composition can be placed directly on a wound site and is fully reabsorbed into the body.

11 Claims, No Drawings

FIBRIN SEALANTS OR ADHESIVES COMPRISING A HYALURONIC ACID DERIVATIVE MATERIAL

CROSS-REFERENCE TO RELATED APPLICATIONS

This application is a continuation of U.S. Application Ser. No. 09/554,745, filed Aug. 14, 2000, now U.S. Pat. No. 6,503,527 as a national stage application under 35 U.S.C. §371 based on International Application No. PCT/US98/24605, filed Nov. 17, 1998, which claims the benefit of the priority date under 35 U.S.C. §119 of U.S. Provisional Application No. 60/065,884, filed Nov. 17, 1997.

BACKGROUND OF THE INVENTION

Fibrin glues, also called fibrin adhesives or sealants, are known for uses in a medical context. Generally, a fibrin glue is obtained by admixing fibrinogen and thrombin containing components. The components are mixed, allowing the thrombin to convert the fibrinogen to fibrin monomers. A number of methods for the production of fibrin glues are known, as illustrated by: Thompson et al., "Fibrin Glue: A Review of Its Preparation, Efficacy, and Adverse Effects as a Topical Hemostat," *Drug Intelligence and Clinical Pharmacy* 22: 946–52 (1988); Brennan, "Fibrin Glue," *Blood Reviews* 5: 240–44 (1991); Stechison, "Rapid Polymerizing Fibrin Glue from Autologous or Single Donor Blood: Preparation and Indications," *J. Neurosurgery* 76: 626–28 (1992); and Toma et al. "Autologous Fibnn Glue in the Repair of Dural Defects in Craniofacial Resections," *J. Laryngology and Otology* 106: 356–57 (1992). (The respective contents of publications cited in this description hereby are incorporated by reference.)

The fibrinogen component of the composition can be obtained by conventional methodology. Examples of such methods include centrifugation, cryoprecipitation and precipitation using polyethylene glycol, ether, ethanol, glycine or ammonium sulfate. Methods of obtaining suitable fibrinogen are disclosed, for example, by Brennan, "Fibrin Glue," *Blood Reviews* 5: 240–244 (1991). Further examples of fibrin components are disclosed in U.S. Pat. Nos. 5,290,918 and 5,395,923.

The thrombin component of the composition is also well known in the art and can be obtained by conventional methods, including recombinant methods. Bovine and human derived thrombins are illustrative of available thrombins well known in the art.

Application of the fibrin glue can be accomplished in a number of ways known in the art. In one method, the admixture is drawn into a syringe and ejected via an appropriate sized needle. In another method a double barrel syringe is used. Other conventional techniques employ a microdrop delivery system, a spray application via a multichannel catheter which is fixed to a pressurized gas source, or a carrier, such as collagen fleece, dura, or a graft. Additionally, a number of special applicators are commercially available.

Numerous uses for fibrin glues are known. Fibrin glues are used in a variety of medical procedures as hemostatic agents, sealants and adhesives. For example, see Chisholm et al., "Fibrin Sealant as a Plug for the Post Liver Biopsy Needle Track," *Clinical Radiology* 40: 627–28 (1989); Toma et al., "Autologous Fibrin Glue in the Repair of Dural Defects in Craniofacial Resections," *J. Latyngology and Otology* 106: 356–57 (1992); Kjaergard et al., "Autologous Fibrin Glue Preparation and Clinical Use in Thoracic Surgery," *Eur. J. Cardio-Thorc. Surg.* 6: 52–54 (1992); Thompson et al., "Fibrin Glue: A Review of Its Preparation, Efficacy, and Adverse Effects as a Topical Hemostat," *Drug Intelligence and Clinical Pharmacy* 22: 946–52 (1988); Brennan, "Fibrin Glue," *Blood Reviews* 5: 240–44 (1991).

Available fibrin glues, however, have a number of significant disadvantages. The fibrinogen and thrombin components must be mixed just prior to use. Admixing too early can result in clotting before it can be applied. Thus, medical professionals are forced to divert their attention for a significant amount of time to prepare the fibrin glue. Early clotting also causes problems in application, such as clogging in the needle or applicator. Additionally, preparation of the fibrin glue can involve complex and time-consuming efforts to establish a workable mix of the fibrinogen and thrombin components. Still further, available fibrin glues may insufficiently adhere to the wound, or may provide inadequate strength to the wound during the healing process.

BRIEF SUMMARY OF THE INVENTION

The present invention relates to a fibrin glue composition comprising a biocompatible and bioabsorbable material, i.e., a biomaterial, of a hyaluronic acid (HA) or a hyaluronic acid derivative. The material may be either nonfilamentous (a film) or a woven or nonwoven fabric. The fibrin glues of the present invention have fibrinogen and thrombin applied to or chemically bonded to the HA or HA derivative material. Additional elements also can be applied to the material. Exemplary of these additional elements are further coagulation factors, anti-fibrinolytics, stabilizers and biologically active substances.

The fibrinogen, thrombin and, optionally, other elements can be applied to the hyaluronic acid derivative film as a dry preparation, as an aqueous or nonaqueous preparation, or as a combination thereof.

BRIEF DESCRIPTION OF THE DRAWING(S)

Not Applicable

DETAILED DESCRIPTION OF THE INVENTION

The present invention relates to a fibrin glue composition comprised of a biocompatible, bioabsorbable hyaluronic acid derivative material, having applied thereto fibrinogen and thrombin. A composition according to the present invention also can contain additional blood coagulation factors, stabilizers, fibrinolysis inhibitors and/or biologically active substances. Factor II and Factor XIII are examples of additional coagulation factors which are suitable for use with the present compositions. Anti-fibrinolytics, such as aprotinin and ε-aminocaproic acid, can also be used. A wide range of biologically active substances are suitable for use with the present invention, including antibiotics, chemotherapeutics, fibroblastic growth factors, angiogenic growth factors, anti-angiogenic growth factors, anti-neoplastic agents, cell growth factors and differentiating agents. Additionally, a suitable source can be added for calcium ions, such as calcium salts.

When placed on a wound site and activated, the compositions of the present invention function as a fibrin glue. In contrast to conventional fibrin glues, however, the inventive compositions do not require complex mixing of fibrinogen and thrombin components immediately prior to use and do not require special applicators.

The compositions of the present invention can be put to a wide range of suitable medical and surgical uses. The compositions can be used in hemostasis applications, as sealants and as adhesives. The compositions of the present invention have a number of surgical uses. In cardiovascular surgery, they can be used as a hemostatic, for example, with needle holes, suture lines, diffuse and nonspecific bleeding, friable tissue bleeding, aortic dissections, ventricular ruptures, and fistulas. In otorhinolaryngology (ear, nose and throat, ENT) surgery, they can be used in facial nerve grafts, closure of dural leaks, nasal septal surgeries, and post tonsillectomy hemorrhage. In neurosurgery, they can be used to prevent cerebral spinal fluid (CSF) leakage, peripheral nerve repair, and to anchor dural patches. In plastic surgery, they can be used in a number of procedures relating to skin grafts, including to fix grafts, control oozing and control bleeding. In thoracic surgery, they can be used, for example, in the treatment of pneumothorax and pulmonary leaks. The compounds of the present invention also have a number of other surgical uses; Illustrative examples include, sealing biopsy needle tracks, liver and splenic lacerations, lymphatic fluid leaks, organ resectioning, seroma and hematoma prevention, and gastrointestinal bleeding. The compositions of the present invention also can be used as a local delivery vehicle for the delivery antibiotics or other biologically active substances to the application site. The compositions of the present invention also may serve as a surgical adhesion barrier. Other uses are known in the art or will be apparent to the skilled artisan.

In one embodiment, the present invention utilizes total or partial cross-linked hyaluronic acid derivatives. These hyaluronic acid derivative compositions can be made in the form of biocompatible and bioabsorbable films. These compositions and methods of making these compositions are disclosed in numerous publications, including U.S. Pat. No. 4,957,744 (Cross-linked Esters of Hyaluronic Acid), U.S. Pat. No. 4,851,521 (Esters of Hyaluronic Acid), U.S. Pat. No. 5,202,431 (Partial Esters of Hyaluronic Acid), and U.S. Pat. No. 5,336,767 (Total or Partial Esters of Hyaluronic Acid). The specific hyaluronic composition can be selected by reference to desired properties, such as hydrophobicity and reabsorption time. The hyaluronic acid derivatives thus employed are formed into films as described in the art. These films can be shaped according to their intended use.

In another embodiment, the present invention utilizes esters of HA. These HA esters typically are formed by treating quaternary ammonium salt of HA with an esterifying agent in a suitable aprotic solvent. Esterification may be carried out using a number of different classes of alcohols such as aliphatic, aryliphatic, cycloaliphatic and heterocyclic. Thus, a number of different derivatives can be synthesized. These derivatives also have a wide range of physicochemical properties. HA esters suitable for use in the present invention are described, for example, by Benedetti et al., "Chemical Modification of Hyaluronan," in *Novel Biomaterials Based in Hyaluronic Acid and Its Derivatives*, Proceedings of a Workshop Held and the Annual Meeting of the European Society for Biomaterials (Pisa, Sep. 10, 1994) (hereafter "1994 *Novel Biomaterials* Proceedings"). See also European Patent 216453 and Benedetti, "New Biomaterials from Hyaluronic Acid," *Medical Device Technology* (November 1994), pages 32–37.

These esters may be formed into various materials, such as fibers, membranes, sponges, fleece-like materials and threads. The fibers may be utilized to produce various fabrics, including woven or nonwoven materials. The membranes also can be made into perforated membranes. Materials comprised of HA esters are detailed by Hellstrom et al., "Endogenous and Exogenous Hyaluronan in Otology," in 1994 *Novel Biomaterials* Proceedings, supra, by Davidson et al., "Biological Response of Experimental Cutaneous Wounds in the Pig to Hyaluronan Ester Biomaterials," loc. cit., by Donati et al., "In Vitro Development and Clinical Application in Burn Patients of Keratinocytes Cultured in a Hyaluronic Acid Ester Membrane," loc. cit, and by Benedetti (1994), supra.

The present invention also contemplates the use of chitin, chitosan and derivatives thereof The chitin, chitosan and derivatives thereof may be formed into various materials, such as films, fibers and membranes. The fibers may be utilized to produce various fabrics, including woven or nonwoven materials. The membranes also can be made into perforated membranes. Materials comprised of chitin, chitosan and derivatives thereof are detailed by Rathke and Hudson, in "Review of Chitin and Chitosan as Fiber and Film Formers," *Rev. Macromol. Chem. Phys.* C34 (3): 375–437 (1994), herein incorporated in its entirety by reference.

The fibrinogen component of the compositions can be obtained by any known method. Examples of such methods include centrifugation, cryoprecipitation and precipitation using polyethylene glycol, ether, ethanol, glycine or ammonium sulfate. Methods of obtaining suitable fibrinogen are disclosed, for example, by Brennan, "Fibrin Glue," *Blood Reviews* 5: 240–44 (1991). Lyophilized fibrinogen, which is particularly suited for use in the present invention, is described in PCT Application WO 9617631 and in U.S. Pat. Nos. 4,909,251 and 4,650,678. Additional fibrinogen containing products suitable for use in the present invention are disclosed in U.S. Pat. Nos. 5,290,918 and 5,395,923.

A thrombin-containing component is a common element of conventional fibrin glues. The thrombin may be derived from any suitable source and obtained by any known method, including recombinant methods. Bovine and human derived thrombins are examples of suitable thrombins. The thrombin can be in powder form and can contain additional elements such as $CaCl_2$.

In addition to or in substitution for thrombin, other fibrinogen-cleaving substances can be employed in the present invention. Illustrative examples of such fibrinogen-cleaving substances include enzymes such as those found in snake venom, for example batroxobin, calobin, fibrozyme and enzymes isolated from the venom of Bothrops jararacussu. See Dascombe et al., "Application of Thrombin Based Fibrin Glue and Non-Thrombin Based Batroxobin Glue on Intact Human Blood Vessels: Evidence for Transmural Thrombin Activity," *Thromb. Haemost.* 78: 947–51 (1997); Hahn et al., "Purification and Molecular Cloning of Calobin, a Thrombin-Like Enzyme from *Agkistrodon Caliginosus* (Korean Viper)," *J. Biochem.* (Tokyo) 119: 835–43 (1996); Fortova et al., "Simultaneous Isolation of Protein C Activator, Fibrin Clot Promoting Enzyme (Fibrozyme) and Phospholipase $A_2$ from the Venom of the Southern Copperhead Snake," *J. Chromatogr. S. Biomed. Appl.* 694: 49–53 (1997); Andriao-Escarso et al., "Isolation and Characterization of a New Clotting Factor from *Bothrops Jararacussu* (Jararacucu) Venom," Toxicon. 35: 1043–52 (1997).

The coagulation factors and other optional components may be applied to the hyaluronic acid derivative material either as a dry preparation, an aqueous or nonaqueous preparation or combination thereof. In one embodiment, the coagulation factors and optional other components are a dry preparation and are applied to the HA or HA derivative material by any suitable method which can achieve uniform application. For example, the coagulation factors and optional other components may be sprayed onto the material. The coagulation factors and optional other components may be applied together or sequentially and in any order.

In another embodiment the fibrinogen and thrombin, as well as any additional constituents that can be suitably sprayed as an aerosol, can be sprayed uniformly over the hyaluronic material, thereby being uniformly applied onto the hyaluronic material.

In yet another embodiment, the coagulation factors and optional other components are chemically bonded to the HA or HA derivative material.

The hyaluronic material, with the fibrinogen, thrombin, and any additional components applied thereto may optionally be sealed. Any suitable, inert coating material can be used to seal the powders onto the film. Examples of such suitable coatings are vitamin based coatings, such as B12- and riboflavin-based coatings.

In alternative to or in combination with a sealing layer, an additional layer may be placed on top of the side comprising the coagulation factors and optional other components. In one embodiment, this additional layer comprises an HA or HA derivative material. The material may be the same or a different formulation than the material onto which the coagulation factors and optional other components are applied or chemically bonded. In another embodiment, the additional layer comprises an HA or HA derivative material that is substantially porous or constructed of a loosely woven fabric, thereby allowing easier activation of the fibrin glue.

The fibrin adhesives and sealants of the present invention have a wide range of medical uses. They are particularly useful where other suturing techniques, such as stitching or stapling, are unsuitable. They can be placed directly on a wound site, and are fully reabsorbed into the body. Where there is a significant amount of blood or other fluid at the site, the fluid will activate the interaction of fibrinogen and thrombin. Where the amount of fluid at the wound site is insufficient, a saline or other suitable solution may be used to activate the composition at the wound site. The fibrin adhesives and sealants of the present invention also are beneficial in absorbing excess fluid at a wound site. Still further, the compositions of the present invention may serve as a surgical adhesion barrier.

From the foregoing description, one skilled in the art can easily ascertain the essential characteristics of the invention and, without departing from the spirit and scope of the invention, can make changes, modifications, and variations of the invention to adapt it to various uses and conditions.

What is claimed is:

1. A method for preparing a bioabsorbable composition, comprising providing a biomaterial which is selected from the group consisting of a hyaluronic acid material, a hyaluronic acid derivative material, a chitin material, a chitosan material, a chitin derivative material and a chitosan derivative material, and treating the biomaterial with fibrinogen and fibrinogen-cleaving agent, wherein the fibrinogen and the fibrinogen-cleaving agent are in a non-activated state.

2. The method of claim 1, wherein the fibrinogen and fibrinogen-cleaving agent are sprayed on the biomaterial.

3. The method of claim 1, wherein the fibrinogen and fibrinogen-cleaving agent are chemically bonded to the biomaterial.

4. The method of claim 1, wherein the fibrinogen and fibrinogen-cleaving agent are sealed to the biomaterial.

5. A bioabsorbable material, comprising a composition which includes fibrinogen, a fibrinogen-cleaving agent and a biomaterial which is a hyaluronic acid material, a hyaluronic acid derivative material, a chitin material, a chitosan material, a chitin derivative material and a chitosan derivative material, wherein the composition is obtained by treating the biomaterial with fibrinogen and the fibrinogen-cleaving agent, and the fibrinogen and the fibrinogen-cleaving agent are in a non-activated state.

6. The material of claim 5, further comprising a sealing layer.

7. The material of claim 5, further comprising an additional biomatetial layer.

8. A method of achieving homeostatis, gluing or wound healing, comprising providing a patient having a site of injury or incision in need of homeostatis, gluing or wound healing, and applying a fibrin adhesive or sealant composition comprising fibrinogen, a fibrinogen-cleavirig agent and a biomaterial which is a hyaluronic acid material, a chitin material or a chitosan material, wherein both the fibrinogen and the fibrinogen-cleaving agent are incorporated on the biomaterial, to the site.

9. The method of claim 8, further comprising adding a saline solution to the composition.

10. A method of achieving homeostatis, gluing or wound healing, comprising providing a patient having a site of injury or incision in need of homeostatis, gluing or wound healing, and applying a biocompatible and bioabsorbable material comprising a biomaterial which is selected from the group consisting of a hyaluronic acid material, a hyaluronic acid derivative material, a chitin material, a chitosan material, a chitin derivative material and a chitosan derivative material; fibrinogen; and thrombin; wherein both the fibrinogen and the thrombin are incorporated on the biomaterial to the site.

11. The method of claim 10, further comprising adding a saline solution to the material.

* * * * *